(12) United States Patent
Juillerat et al.

(10) Patent No.: US 7,597,904 B2
(45) Date of Patent: *Oct. 6, 2009

(54) METALLOPROTEINASE INHIBITORY AGENT

(75) Inventors: Marcel-Alexandre Juillerat, Lausanne (CH); Marie-Claude Robert, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/739,368

(22) Filed: Apr. 24, 2007

(65) Prior Publication Data

US 2007/0258914 A1 Nov. 8, 2007

Related U.S. Application Data

(63) Continuation of application No. 10/978,319, filed on Oct. 28, 2004, now Pat. No. 7,258,996.

(51) Int. Cl.
*A23C 9/123* (2006.01)
*A23C 9/127* (2006.01)
*A61K 38/10* (2006.01)
*C07K 7/08* (2006.01)

(52) U.S. Cl. .................. 424/439; 424/442; 426/43; 426/580; 435/71.2; 514/13; 514/14; 530/326; 530/327; 530/343

(58) Field of Classification Search .............. None
See application file for complete search history.

(56) References Cited

U.S. PATENT DOCUMENTS

| | | | |
|---|---|---|---|
| 5,866,357 | A | 2/1999 | Dambmann et al. |
| 6,500,798 | B1 | 12/2002 | Stanton et al. |
| 6,908,633 | B2 * | 6/2005 | Hayasawa et al. ............. 426/34 |
| 7,258,996 | B2 * | 8/2007 | Juillerat et al. ............. 435/68.1 |
| 2002/0147144 | A1 | 10/2002 | Sidelman |
| 2003/0144179 | A1 | 7/2003 | Takahasi et al. |

FOREIGN PATENT DOCUMENTS

| | | |
|---|---|---|
| JP | 4341193 | 11/1992 |
| WO | WO 94/28126 A2 * | 12/1994 |
| WO | WO 99/65326 | 12/1999 |
| WO | WO 01/68672 A1 * | 9/2001 |
| WO | WO 01/84948 | 11/2001 |
| WO | WO 91/13554 | 4/2007 |

OTHER PUBLICATIONS

Schieber, A. et al., "Characterization of Oligo and Polypeptides Isolated From Yoghurt," European Food Research and Technology, vol. 210, No. 5, pp. 310-313 (2000) XP 001106138.
Kohmura, M. et al., "Inhibition of Angiotensin-Converting Enzyme Bu Synthetic Peptide Fragmetns of Various Beta Caseins," Agricultural and Biological Chemistry, vol. 54, No. 4, pp. 1101-1102 (1990) XP 001106729.
Otani, H. et al., "Studies on the Antigenic Structure of Bovine Beta Casein VI. Antigenic Activities of Peptides Produced By Tryptic and V8-Proteolytic Digestions of Peptide 110-144," Milchwissenschaft, vol. 43, No. 12, pp. 759-761 (1988) XO001106112.
Eigel et al., "Nomenclature of Proteins of Cow's Milk: Fifth Revision," Journal of Dairy Science, vol. 67, No. 8, pp. 1599-1631 (1984).
Enomoto et al., Antibodies Raised Against Peptide Fragments of Bovine alpha s1-Casein Cross-React With the Intact protein Only When the Peptides Contain Both B and T Cell Determinants; Molecular Immunology, vol. 27, No. 6, pp. 581-586 (1990).
Hegazi, "Proteolytic activity of lactic acid bacteria in skim milk with special reference to the biodegradation of casein fractions," Die Nahrung, vol. 31, pp. 19-26 (1987).
Meisel et al., "Bioactive peptides encrypted in milk proteins: proteolytic activation and thropho-functional properties," Antoine van Leeuwenhoek, vol. 76, pp. 207-215 (1999).
Robert et al., "Generation of Bioactive Peptides Derived from Caseins Using a Lactobacillus helveticus Strain," Proceedings of the Second International and the Seventeenth America Peptide Symposium, American Peptide Society, pp. 770-771 (2001).
Yamamoto et al., "Antihypertensive Effect of the Peptides Derived from Casein by an Extracellular Proteinase from Lactobacillus helveticus CP790," Journal of Dairy Science, vol. 77, No. 4, pp. 917-922 (1994).

* cited by examiner

*Primary Examiner*—Jeffrey E Russel
(74) *Attorney, Agent, or Firm*—K&L Gates LLP

(57) ABSTRACT

The present invention relates to an active agent, in particular a metalloproteinase inhibitory agent of casein-derived peptides obtained by hydrolysis of casein by a food grade bacteria. The invention also relates to the manufacture of an active agent, in which a food grade bacteria of the genus *Lactobacillus helveticus* is contacted with casein in order to perform a hydrolysis and obtain casein-derived peptides exhibiting metalloproteinases inhibitory property. The present invention also includes isolated and purified inhibitory peptides obtained by hydrolysis of casein by the bacteria.

12 Claims, 1 Drawing Sheet

METALLOPROTEINASE INHIBITORY AGENT

CROSS-REFERENCE TO RELATED APPLICATIONS

This application is a continuation of patent application Ser. No. 10/978,319, filed Oct. 28, 2004, which is a continuation of International application PCT/EP03/03663 filed Apr. 8, 2003, the entire contents of which are expressly incorporated herein by reference thereto.

BACKGROUND

The present invention relates to an active agent and, in particular, to a proteinase inhibitory agent. More specifically, this invention relates to metalloproteinase inhibitory agent comprising casein-derived peptides.

The degradation of extracellular matrix (ECM) is a very complex process and is part of many pathological and physiological processes. The proteolytic degradation of the extracellular matrix therefore plays a crucial role in cancer invasion as in non-neoplastic tissue remodeling processes. The role of the matrix-metalloproteinases (MMPs) enzymes in the tumor cell-mediated extracellular matrix proteolysis is well established. Thus, by regulating composition and integrity of ECM, MMPs play an important role in the control of signals elicited by matrix molecules and regulate cell proliferation, differentiation and cell death. MMPs are ubiquitous enzymes and prostate, breast, bone as well as colon tumor cell lines have been shown to secrete MMPs in vitro. The MMP family has over 20 members that cleave various components as various as fibronectin, gelatin and collagen for example. Among the MMPs family, MMP-2 and MMP-9 have been identified in cancer cells and the active forms were detected more frequently in malignant than in benign breast carcinoma. MMP-2 may thus be considered as a key enzyme in ECM remodeling involved in tumor invasion and metastasis.

Beyond cancer and tumor invasion, MMPs are also associated with a wide variety of normal and pathological conditions involving matrix degradation and remodeling. MMPs are thus involved in some physiological processes like foetal development, angiogenesis, bone formation and resorption. Indeed, bone resorption models showed that MMP-9 is specifically required for the invasion of osteoclasts and endothelial cells into the discontinuously mineralized hypertrophic cartilage that fills the core of the diaphysis. MMPs have also been reported to be involved in pathological processes like artherosclerosis, arthritis, autoimmune diseases, periodontitis, tissue ulceration and of course cancer invasion and metastasis.

It is also known that the proteolytic activity of the MMPs involved in ECM degradation may be regulated by their endogenous inhibitors, the tissue inhibitors of metalloproteases (TIMPs). These inhibitors influence the activation of the metalloproteases and act to modulate proteolysis of ECM, notably during tissue remodeling and inflammatory processes. There are also synthetic inhibitors like marimastat for example, a butanediamide derivative with an IC50 in the micromolar range. Inhibitors of MMPs generally fall into three pharmacological categories: collagen peptidomimetics and non-peptidomimetics, tetracyclin derivatives and bisphosphonates.

MMPs inhibitors would therefore have the potential to inhibit tumor growth by preventing local invasion and by inhibiting tumor angiogenesis. The current existing non-endogenous inhibitors present the drawback of a poor oral bioavailability as well as high cost. Moreover since these are synthetic molecules, the synthesis route is generally cumbersome and necessitates purification step in order to recover functional mixtures.

Therefore, there remains a need for a simple procedure for obtaining a metalloproteinase inhibitory agents that would be inexpensive and easy to prepare and that could also be used in a food product or as a neutraceutical additive. The present invention now satisfies this need.

SUMMARY

The present invention relates to a method for inhibiting metalloproteinases, preferably matrix-metalloproteinases. This is accomplished by providing an inhibitory agent that is effective for this purpose, the agent comprising casein-derived peptides obtained by hydrolysis of casein by a food grade bacteria.

The present invention also concerns the use of the inhibitory agent according to the present invention, systematically, locally or topically for inhibition of metalloproteinases, in particular matrix-metalloproteinases.

Another aspect of the present invention relates to the manufacture of a metalloproteinases inhibitory agent, in particular a matrix-metalloproteinases inhibitory agent, comprising the steps of:

preparing a solution of casein and food grade bacteria, holding the solution under conditions effective to partially hydrolyze the casein to provide a metalloproteinases inhibitory agent containing casein-derived peptides, and stopping the hydrolysis to form the agent.

Advantageously, the inhibitory agent is recovered from the solution prior to further use.

BRIEF DESCRIPTION OF THE FIGURES

FIG. 1 describes peptide sequences (SEQ ID NOS. 1-17) from RP-HPLC analysis of preferred metalloproteinases inhibitory agents illustrating a common amino acid sequence.

DETAILED DESCRIPTION

The expression "food grade bacteria" refers to any bacteria that have no harmful effect on human health or that have a GRAS (generally recognized as safe) status. Such bacteria maybe selected from the group consisting of Lactobacilli and Bacilli. The preferred bacteria particularly suitable for the purpose of the process according to the present invention may be *Lactobacillus helveticus* ssp, more particularly *Lactobacillus helveticus* deposited under the No. I-2864 at CNCM, under the Budapest Treaty with the Institut Pasteur, 28 Rue du Dr Roux, F-75724 Paris, on Apr. 29, 2002.

The present invention also relates to the manufacture of a metalloproteinases inhibitory agent, in which isolated proteolytic enzymes of the preferred food grade bacteria are used instead or in combination with the bacteria.

A further aspect of the present invention relates to the manufacture of a fermented dairy product containing a metalloproteinases inhibitory agent, preferably matrix-metalloproteinases inhibitory agent, comprising the steps of:

contacting lactic acid bacteria with milk, and fermenting the obtained mixture to obtain a fermented dairy product, under conditions to partially hydrolyze the casein of the milk into casein-derived peptides to provide a fermented dairy product containing a metalloproteinases inhibitory agent, in particular a matrix-metalloproteinases inhibitory agent.

Thus, the present invention provides inhibitors of metalloproteinases, in particular matrix-metalloproteinases, in the form of single-polypeptide-chain peptides. The particularly preferred inhibitors according to the present invention are selected from the group consisting of the single-polypeptide-chain peptides set forth in SEQ ID NO 1 to 8, having the amino acid sequence:

E-N-L-L-R-F-F-V-A-P-F-P-E-V-F,  (SEQ ID NO: 1)

E-N-L-L-R-F-F-V-A-P-F-P-E-V-F-G-K-E-K-V,  (SEQ ID NO: 2)

N-E-N-L-L-R-F-F-V-A-P-F-P-E-V-F,  (SEQ ID NO: 3)

L-N-E-N-L-L-R-F-F-V-A-P-F-P-E-V,  (SEQ ID NO: 4)

E-N-L-L-R-F-F-V-A-P-F-P-E,  (SEQ ID NO: 5)

N-E-N-L-L-R-F-F-V-A-P-F-P-E,  (SEQ ID NO: 6)

G-L-P-Q-E-V-L-N-E-N-L-L-R-F-F,  (SEQ ID NO: 7)
and

F-V-A-P-F-P-E-V-F-G-K-E-K-V-N-E-L-S-K-D-I-G-S  (SEQ ID NO: 8)

and substantially homologous variants thereof.

Other particularly preferred inhibitors according to the present invention are selected from the group consisting of the single-polypeptide-chain peptides set forth in SEQ ID NO:9 to 17, having the amino acid sequence:

L-H-L-P-L-P-L-L)  (SEQ ID NO: 9)

L-H-L-P-L-P-L-L-Q  (SEQ ID NO: 10)

N-L-H-L-P-L-P-L-L-Q  (SEQ ID NO: 11)

N-L-H-L-P-L-P-L-L  (SEQ ID NO: 12)

N-L-H-L-P-L-P-L-L-Q-S-W  (SEQ ID NO: 13)

D-V-E-N-L-H-L-P-L-P-L-L-Q-S-W  (SEQ ID NO: 14)

V-E-N-L-H-L-P-L-P-L  (SEQ ID NO: 15)

V-E-N-L-H-L-P-L-P  (SEQ ID NO: 16)
and

L-P-L-L-Q-S-W-M-H-Q-P-H-Q-P-L-P-P-T-V-M-F-P-P-Q-S  (SEQ ID NO: 17)

substantially homologous variants thereof.

The expression "substantially homologous" as used herein means a degree of homology in excess of 70%, and preferably in excess of 80%.

The amino acids represented by the foregoing abbreviation are set forth below in this detailed description of the preferred embodiments.

The present invention also concerns the use of the inhibitors according to the present invention, systematically, locally or topically for inhibition of metalloproteinases, in particular matrix-metalloproteinases.

It is yet an other aspect of the present invention to provide pharmaceutical composition comprising an amount of inhibitors of metalloproteinases, in particular matrix-metallopro-teinases, effective to reduce activities and/or functions of such metalloproteinases, in particular matrix-metalloprotein-ases.

Furthermore, other biologically active, improved analogs of the metalloproteinases inhibitors of the present invention may be obtained by replacing various other amino acids in the inhibitor amino acid sequence.

In the present context, the term "metalloproteinase" embraces any kind of metal dependant proteolytic enzymes. Therefore, this term encompasses the matrix-metalloproteinases as described in the introduction of the present application such as MMP-1, MMP-2, MMP-3, MMP-4, MMP-5, MMP-6, MMP-7, MMP-8, MMP-9, MMP-10, MMP-11, MMP-13, MMP-14, MMP-15, MMP-16, MMP-17, MMP-18, MMP-19, MMP-20, MMP-21, MMP-22, MMP-23, MMP-24, MMP-25, MMP-26, MMP-27, and MMP-28. However, it also concerns other metal dependant proteinases like angiotensine converting enzyme (ACE), endothelium converting enzyme (ECE) and neutral endopeptidase since all these enzymes work according a similar chemical mechanism.

It has thus been surprisingly found that such agent shows a noticeable proteolytic inhibitory effect regarding metalloproteinases activity, and particularly regarding matrix metalloproteinases activity. The present invention encompasses also the use of the inhibitors according to the present invention or composition comprising casein-derived peptides obtained by hydrolysis of casein by a lactic acid bacteria for the inhibition of metalloproteinases, particularly matrix metalloproteinases.

The inhibitors and inhibitory agent according to the present invention may be used for inhibition of metalloproteinases, particularly matrix-metalloproteinases, and therefore applied for inhibition of cancer invasion and metastasis, tissue ulceration, arthritis and periodontitis as well as inhibition of osteoclasts.

Such an agent is particularly suitable for use in food products, such as fermented and non-fermented dairy products like yogurts or fermented dairy beverages, for example.

Such agent may also be used in chewing gum, candies or oral supplements, for example, for the local inhibition of metalloproteinases, in particular matrix-metalloproteinases, involved in periodontitis. In a similar way of use, the agent according to the invention may also be used in toothpaste or mouth-bath, for example, for the same purpose. The present agent may also be advantageously used in pet foods or treats for pets, for example. Indeed, a particular pet disease called Feline Osteoclastic Resorptive Lesion is suspected to be induced by local over-activity or activation of matrix-metal-loprotease on the jaws of cats. The proteases thus activated induce the resorption of jawbone that will finally lead to loss of teeth and dental-incapacity of the pets, particularly cats. Therefore the local use of the inhibitors or inhibitory agent according to the present invention for reducing feline osteoclastic resorptive lesions presents a preferred aspect of the present invention.

Figure 1:
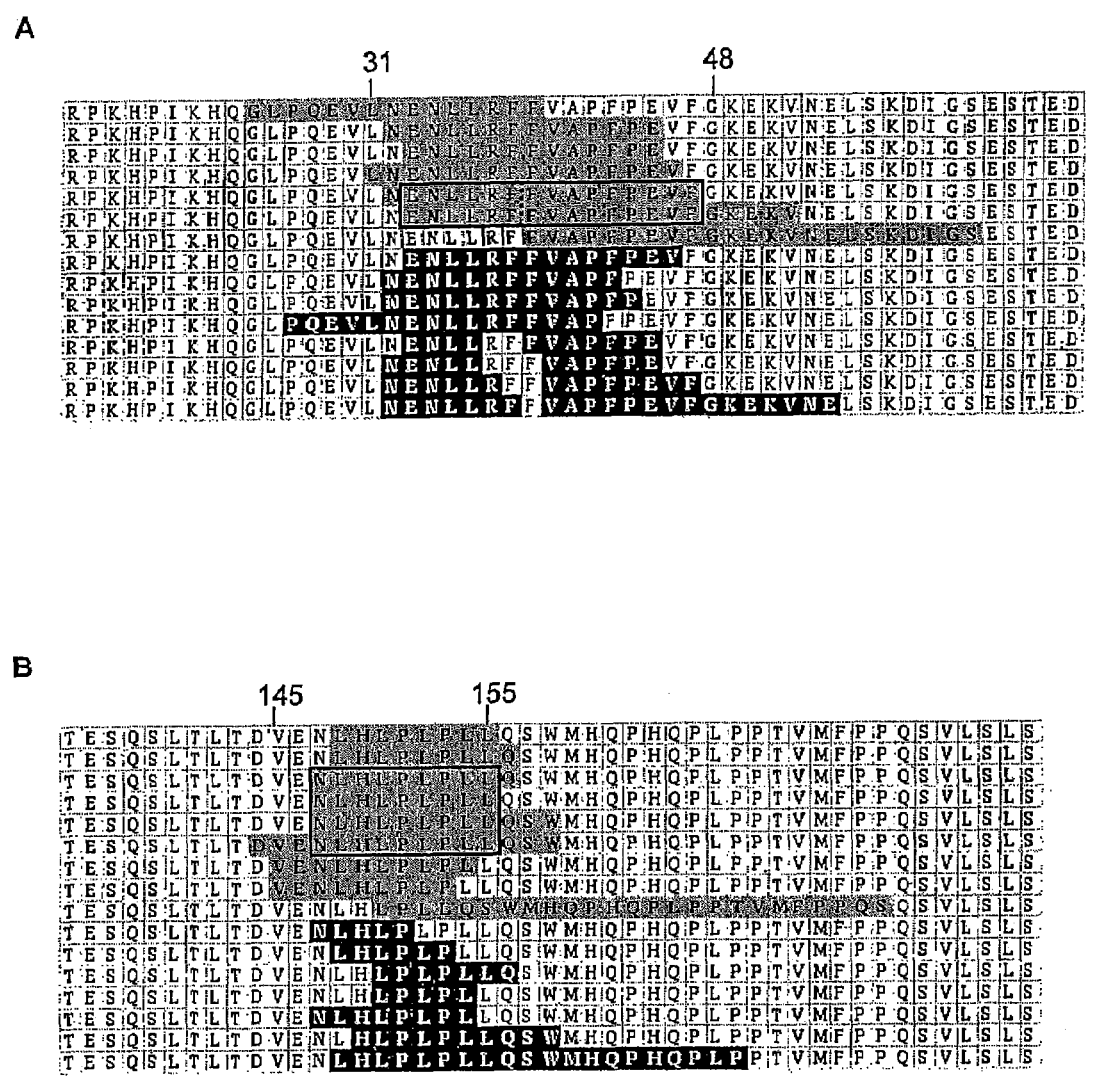

FIG. 1 describes peptide sequences from RP-HPLC subfractions 24-27 of fraction 6 from GPC showing a common amino acid sequence. Peptides from the candidate region retrieved in inactive fraction are shown in black whereas peptides characterized in subfractions twenty-four to twenty-seven and showing activity are shown in gray. A refers to Alpha-casein and B refers to Beta-casein.

Material and Methods

HPLC/Mass Spectrometer

Finnigan Mat ion-trap LCQ mass spectrometer (Thermo Finnigan, San Jose, Calif., USA)

Finnigan Mat Spectra System P4000 (Thermo Finnigan, San Jose, Calif., USA)

Finnigan Mat Spectra System AS3000 (Thermo Finnigan, San Jose, Calif., USA)

SEQUEST developed by John Yates and Jimmy Eng at the University of Washington and is protected by U.S. Pat. No. 5,538,897

Agilent 1050 Series Modules and Systems for HPLC (Agilent Technologies, Palo Alto, Calif., USA)

Columns for HPLC/MS

Superdex 75 HR 10/30 (Amersham Pharmacia Biotech, Duebendorf, Switzerland)

Column C8, 208TP54, pore size: 300 Å, particle size: 5 µm, inner diameter: 4.6 mm, length: 250 mm (Vydac, Hesperia, Calif., USA)

Nucleosil C18, pore size: 100 Å, particle size: 5 µm, inner diameter: 1 mm, length: 250 mm (Macherey-Nagel AG, Oensingen, Switzerland)

Preparative C18, 218 TP152050, pore size: 300 Å, particle size: 10-20 µm, inner diameter: 50 mm, length: 250 mm (Vydac, Hesperia, Calif., USA).

Peptide Synthesis

ACT 348 Omega Multiple Peptide Synthesizer (Advanced ChemTech Inc, Louisville Ky., USA)

Culture of Lactic Acid Bacteria

Bacteria were grown without shaking, overnight in sterile MRS broth at 40° C. in a water bath. UHT-skim milk was inoculated at 2% from the overnight MRS culture and fermentation occurred at 37° C. Bacteria were finally harvested as the pH of the fermented milk lied below 4.5. The pH of the fermented milk was readjusted to 5.2 with NaOH and 2% of tri-sodium citrate were added to solubilize the caseins. The fermentation solution was allowed to rest for 10 min at RT.

Subsequently, bacteria were centrifuged at 3,700 g, 4° C. during 10 min, washed 3 times and resuspended in tris-maleate buffer.

The optical density of the suspension was measured, assuming that the increase in cell suspension turbidity of 1.0 unit of absorbance at 600 nm corresponds to $10^8$ cells/ml.

Buffer: Tris-maleate (30 mM): 3.63 g tris(hydroxymethyl)-aminomethane, 3.48 maleic acid and 2.94 calcium chloride were added to 1 liter $H_2O$ and the pH was adjusted to 7.5 with NaOH.

Casein Hydrolysis with Lactic Acid Bacteria

The equivalent of OD=80 or 8*109 cells per ml (final conc.) bacteria were incubated at 37° C. in a water bath with sodium caseinate (4 mg/ml) in 30 mM tris-maleate buffer. Samples were taken as a function of time (maximum: 5 hours). The proteolysis was stopped by centrifugation at 14,000 g and the supernatant was recovered. The samples were conserved frozen at −20° C. for subsequent analyses.

Buffer: Tris-maleate (30 mM): 3.63 g tris(hydroxymethyl)-aminomethane, 3.48 maleic acid, 2.94 calcium chloride were mixed, the pH adjusted with NaOH to 7.5 and the solution completed to 1 liter with $H_2O$.

Casein Antigenicity ELISA Test

Microtitration plates were coated with caseinate in coating buffer at a concentration of 50 µg/ml and incubated overnight at 4° C.

Four washing steps with phosphate buffered saline-Tween-20 solution were performed before each successive reagent addition. The unoccupied sites were blocked with fish gelatin buffer during 30 min. Test samples dilutions and a standard solution were mixed with rabbit anti-casein IgG-polyclonal antibodies (dilution 1:10,000) and incubated for 1 hour at RT. A peroxidase labeled second antibody (dilution 1:2,000) was then added and incubated for 30 min. Subsequently, the reaction substrate (o-phenylene-diamine, OPD) was added for 5-10 min and the reaction stopped with 5% $H_2SO_4$ (final conc.). The plate was read at 490 nm.

Coating buffer: 795 mg $Na_2CO_3$ and 1.465 g $NaHCO_3$ were added to 500 ml H2O (pH 9.6).

PBS buffer: 8 g NaCl, 200 mg $KH_2PO_4$, 200 mg KCl and 2.9 $Na_2HPO_4$ dodecahydrate were added to 1 liter $H_2O$.

PBS-Tween 20: 0.25 g Tween-20 were added to 1 liter PBS.

Fish gelatin buffer: 0.5% fish gelatin in PBS buffer.

Substrate buffer: 0.51 g citric acid, monohydrate and 1.84 g $Na_2HPO_4$ were added to 100 ml $H_2O$. 15 minutes before use 40 mg OPD, and finally 40 µl Perhydrol® were added.

Leucine Aminopeptidase Activity Test

The leucine aminopeptidase activity was measured according to the procedure described by Sarath et al (Sarath, G., R. De La Motte, and F. W. Wagner. 1989. *Protease assay methods. In Proteolytic enzymes: A practical approach.* R. J. Beynon and J. S. Bond, editors. IRL Press, Oxford. 25-56) with some modifications. The assay was performed in a microtiter plate. In each well, 180 µl of 100 mM phosphate buffer, pH 6.5, 10 µl enzyme solution and 10 µl H-Leu-pNA (10 mM in DMSO) were mixed and incubated at 37° C. for 1 hour. The absorbance at 405 nm was measured as a function of time (molar absorption coefficient, $\epsilon=10,500\ M^{-1}cm^{-1}$).

Initial velocities are proportional to the enzyme concentration. The difference in absorbance $\Delta A_{400}$ is equivalent to the absorbance read during the enzymatic reaction minus the absorbance from the blank reaction (negative control).

The result is expressed in µmol p-nitroaniline formed per ml enzyme solution per minute [U/ml].

One leucine aminopeptidase unit (LAPU) is defined as the amount of enzyme required to liberate one micromole of p-nitroaniline per minute at 37° C.

Enzymatic Hydrolysis of an Active Fraction from Sodium Caseinate Hydrolysate

Fractions showing antiproliferative character were hydrolysed in a first step with 1% alcalase for 1 hour at 55° C. in a thermomixer at 600 rpm. In a second step, the hydrolysate was incubated with 1% acid proteinase A for 1 hour at 50° C. in a thermomixer at 600 rpm. The enzymatic reaction was stopped heating the sample 5 minutes at 95° C. Enzymes were finally removed from the hydrolysate using Ultrafree®-0.5 centrifugal filter units having a nominal molecular weight limit of 10,000 Da.

Percentages of enzyme given here represent the enzyme proteinic content vs. the hydrolysate proteinic content.

Culture of Human Intestinal Epithelial Cells (IECs) and Proliferation Assay

Human colonic adenocarcinoma cell line HT29 (ATCC: HTB-38) from the American Type Culture Collection (ATCC, Manassas, Va.).

DMEM, high glucose (4.5 g/l), with stable glutamine (BioConcept, AMIMED, Allschwil, Switzerland)

Undifferentiated cells (passages 45-78) were maintained in glucose-containing DMEM supplemented with 10% FCS at 37° C. in a 5% CO2/air incubator. Culture medium was changed every two days until the cell monolayers reached 50% confluence. For stimulation assays, HT-29 cells were plated at $1.2*10^4$ cells/well in 96-well flat-bottom plates. After incubation for 4 days, the amount of cells present in the wells before incubation with the samples was assessed adding neutral red solution in 4 wells and incubating the plate for 45 min. The HT-29 cells were then washed twice with serum-free media (inclusive the wells with neutral red solution). The wells colored with neutral red remained from now on free of any media.

HT-29 cells were then incubated 24 hours respectively in the presence of 80 µg (hydrolysed) sodium caseinate samples in 200 µl DMEM, in 200 µl serum-free medium (blank), in 200 µl medium with serum (positive control) or in 0.9% saline solution (negative control). After incubation, the cells were washed twice with serum-free media, neutral red solution was then added and the cells incubated for 45 min. All wells were washed three times with saline water and residual solution was removed hitting the plate gently on a tissue. The dye was finally extracted with 100 µl of an extraction solution and the optical density measured at 540 nm. The optical density measured correlates with the number of cells present in the wells.

The proliferation was calculated by the difference in absorbance between the cells having been incubated 24 hours with sodium caseinate samples, with serum-free medium, with medium containing serum or with 0.9% saline solution and the cells before incubation.

The difference in absorbance $\Delta A_{540}$ from the blank (cells incubated with serum-free medium) was normalized. The results were then expressed as percentage with respect to the blank.

- Culture medium with serum: DMEM was supplemented with 10% decomplemented FCS and 1% Penicillin-Streptomycin. The solution was sterile filtered Ø22 µm.
- Culture medium, serum-free: DMEM was supplemented with 1% Penicillin-Streptomycin. The solution was sterile filtered Ø22 µm
- Extraction solution: 1% acetic acid, 50% EtOH in water.
- Neutral red stock solution: 617 mg of Neutral Red were dissolved 100 ml in 0.9% NaCl solution. The solution was autoclaved at 120° C. for 15 min and stored at 4° C. in light-shielded bottles.
- Neutral red solution: Dilute 3:10 Neutral Red stock solution in DMEM, serum-free. Use this solution for the assay.
- Foetal calf serum (FCS) was decomplemented during 30 min at 56° C.

Lactate Dehydrogenase Cytotoxicity Test

Cell viability was rigorously measured according the manufacturer's recommendations (Roche Diagnostics). The test is based on the measurement of lactate dehydrogenase (LDH) activity released from the cytosol of damaged cells in the supernatant.

Hydrolysate Fractionation by Gel Permeation

Samples were analyzed using a Superdex 75 column with an isocratic elution using 50 mM ammonium acetate, pH 7, as solvent for 65 min. The flow rate was 0.5 ml/min, at pressure of 17-19 bar. Detection was accomplished at 280 and 215 nm.

Prior separation, the samples were heated for 5 min at 90° C. and centrifuged at 14,000 g in a bench centrifuge. 100 µl supernatant were then injected for analysis and separation. Fractions were collected as a function of their molecular weight.

Finally, the collected fractions were lyophilized and resuspended in $H_2O$ twice before final lyophilization. This procedure should ensure the disappearance of any traces of ammonium acetate.

HPLC-solvents were sterile-filtered (Ø22 µm) and sonicated at least 5 minutes to remove any air bubbles.

Hydrolysate Fractionation by Reverse-Phase Chromatography, Using a C8 Column

Since 100 µl caseinate hydrolysate had been fractionated on the Superdex75 column, the resulting lyophilized gel permeation fractions were resuspended in 100 µl $H_2O$ for testing the inhibition of cell proliferation. The concentration of each peptide in a fraction was thus comparable to the concentration of the peptide in the initial hydrolysate sample.

Samples (100 µl) with a molecular weight between 5,000 and 1,000 Da were analyzed using a C8-column with a linear gradient increase of solvent B in solvent A as follows: 5 minutes isocratic elution at 0% B, 0-50% B in 60 minutes, 50-100% B in 1 minute, 4 minutes at 100% B, change to 100% A in one minute and finally re-equilibration at 100% A during 9 minutes.

Samples (100 µl) with a molecular weight lower than 1,000 Da were analyzed using a C8-column with a linear gradient increase of solvent B in solvent A as follows: 5 minutes isocratic elution at 0% B, 0-35% B in 60 minutes, 35-100% B in 1 minute, 4 minutes at 100% B, change to 100% A in one minute and finally re-equilibration at 100% A during 9 minutes.

Total time run for both analyses was 80 min and the flow rate amount to 0.8 ml/min with a pressure of 105-120 bar. The injection volume was 100 µl Following chromatographic separation, fractions were collected every 2.5 min (2 ml volume). The collected fractions were lyophilized and resuspended in $H_2O$ twice before final lyophilization. This procedure should ensure the disappearance of any traces of trifluoroacetic acid.

Finally, the lyophilized fractions were resuspended in 100 µl $H_2O$ to ensure that the concentration of each peptide before fractionation is the same after fractionation.

HPLC-solvents were sterile-filtered (Ø22 µm) and sonicated at least 5 minutes to remove any air bubbles.

Solvent A: 0.05% TFA in water
Solvent B: 0.045% TFA, 80% acetonitrile in water

ESI-MS/MS

Peptides separated by GPC methods were characterized using a SpectraSystem HPLC with a C8 or a C18 column coupled to the Finnigan LCQ ion trap mass spectrometer equipped with an ESI source. The HPLC system consisted of a quaternary pump (TSP P4000), an autosampler (TSP AS3000) and a UV/VIS detector (UV/VIS 205 from Linear Instruments) equipped with a high pressure flow-cell (1.6 µl volume, 2 mm pathlength). HPLC flow was directed via 0.005" ID PEEK tubing to a micro flow-splitter with 10% going to the MS and 90% being collected in a fraction collector. The MS instrument was tuned and calibrated using the manufacturer's protocols (ThermoFinnigan). The ESI source was operated at 4.5 kV and the interface capillary heater was set to 200° C. Sheath gas flow was maintained at flow rates of 50 ml/min.

All spectra were obtained in positive mode and recorded at unit-mass resolution. Automated MS/MS spectra were acquired with relative collision energy for CID preset at 35% and an isolation width of 1 m/z units. During an automated run, if an ion was present in a scan above a specified threshold, a product ion spectrum was acquired. After two product ion spectrum scans of the most abundant ion, it was excluded to trigger further MS/MS scans ("dynamic exclusion" option in Xcalibur software package). The second most abundant ion, if still above specified threshold, could trigger again product ion spectrum acquisition. Dynamic exclusion allowed the generation of MS/MS spectra of peptide mixtures in peaks not fully resolved by chromatography. The mass spectrometer continued to alternate between MS and MS/MS mode until the ion intensity dropped below the threshold. The scan range was set at m/z 150.0-2000.0.

Data Analysis

Full scan MS and MS/MS data acquisition and analysis was performed with Xcalibur software V1.0 SR1 (Finnigan), including Bioworks V1.0 software package for SEQUEST™ database searches.

Experimentally obtained peptide masses were compared to SwissProt protein database using PeptIdent (Peptide Mass Fingerprinting) and PeptideMass programs accessible from the ExPASy Molecular Biology Server of the Swiss Institute of Bioinformatics.

MSMS spectra analysis was performed using the SEQUEST™ program. It correlates uninterpreted MSMS spectra of peptides with amino acid sequences from protein and nucleotide databases. Based on this correlation it determines the amino acid sequence and thus the protein(s) that correspond to the mass spectrum being analyzed.

Peptide Synthesis Procedure

All peptides (400-500 mg) were synthesized on an Advanced Chemtech peptide synthesizer ACE 348 omega. The α-amino function of the amino acids was protected with the base labile fluorenyl methoxy carbonyl (Fmoc) and side chains of tri-functional amino acids with acid labile protecting groups, i.e. Arg(Boc)2, Glu(Otbu), His(Trt) and Asn (Mtt).

In general, prior to peptide synthesis, the resin was swollen in dichloromethane (DCM) during 30 min. Peptides were assembled by sequential amino acid coupling on Sasrin resin applying the Fmoc-strategy[180] According to the published procedures of automated peptide synthesis, a deprotection/coupling cycle comprises I) a 10 min deprotection of Fmoc amino acid derivative (2 eq) in DMF with Benzotriazol-1-yl-oxy-tris(pyrrolidino)phosphonium hexafluorophosphate (PyBOP, 2.5 eq) as coupling reagent and N,N-diisopropyl ethylamine (DIEA, 5 eq) as base.

Cleavage of the peptide from the resin was performed with 2% trifluoroacetic acid (TFA) in DCM during 20 min. After treatment, the resin was separated by filtration and the filtrate concentrated in vacuo. For complete removal of the side chain protection, the peptide was treated with a cocktail of TFA/Triisopropylsilan (TIS)/water (90:5:5, v/v). After 1 hour, cold diethyl ether was added to precipitate the product. The precipitate was collected by centrifugation and lyophilized from a water/acetonitrile (1:1, v/v) solution to afford a colorless solid.

After lyophilization, the crude product was purified by preparative RP-HPLC on a C18-column applying a linear gradient from 20% A to 60% A (A: 0.9% TFA in acetonitrile, B: 10% A in $H_2O$) over 30 min at flow rate of 80 ml/min. The eluate was monitored by UV absorption at 214 nm wavelength, appropriate fractions were collected and lyophilized. The peptide was characterized by electrospray ionization mass spectrometry (ESI-MS) and analytical RP-HPLC.

Angiotensin-Converting-Enzyme Inhibitory Test

This procedure is a rapid spectrophotometric method utilizing the synthetic tripeptide substrate N-[3-(2-furyl)acryloil]-L-phenylalanylglycylglycine (FAPGG). $K_m$-value: 0.3 mM.

FAPGG was hydrolysed to furylacryloylphenylalanine (FAP) and glycylgylcine. Hydrolysis of FAPGG resulted in a decrease in absorbance at 340 nm.

The ACE reagent and the ACE Calibrator were reconstituted according to the manufacturer's recommendations.

The assay was performed in quartz cuvets. 0.05 ml ACE Reagent Solution, 0.05 ml casein hydrolysate and 0.05 ml ACE calibrator were mixed and incubated at 37° C. for 10 minutes.

The absorbance at 340 nm was measured as a function of time.

The ACE activity in the sample was determined by comparing the sample reaction rate to that obtained with the ACE calibrator. The results are expressed as percentage with respect to the control.

Matrix Metalloproteinase Inhibitory Test

The assay was performed in microtiter plates. In each single well 1 µl enzyme, the inhibitor at the desired concentration and finally 5 µl substrate were added to PBS buffer (pH 7.0-7.5), final volume: 200 µl. The reaction mixture was incubated at 37° C. for 2 hours. The increase in fluorescence was continuously recorded, exciting at 485 nm and reading the emission at 530 nm, with a gain of 40.

Inhibitors:— o-phenantroline: 9.9 mg in 25 µl DMF (dimethylformamide→add 1 µl (final concentration: 10 mM)

synthetic inhibitors at different concentrations

Substrate: DQ-gelatin: 1 mg/ml in PBS→add 5 µl to the reaction (reaction volume: 200 µl) (final concentration: 25 mM)

Enzymes:

MMP-7: stock solution: 1 U/µl

MMP-2: stock solution: 0.05 µg/µl

MMP-9: stock solution: 0.05 µg/µl

Results & Discussion

Generation of the Peptide Library with *Lb. helveticus* CNCM I-2864 . . .

Following preliminary trials with several LAB representing the variety of LAB used in dairy products, the *Lb. helveticus* CNCM I-2864 strain was selected to hydrolyze sodium caseinate in a buffered system. Caseinate hydrolysis occurred at 37° C. for 5 hours. Samples were taken as a function of the time and proteolysis was stopped by centrifugation of the bacteria and recovery of the supernatant. The caseinate hydrolysates taken at different times constituted the peptide libraries studied below.

Leucine Aminopeptidase Test

This test was performed to check that caseinate hydrolysis was the action of the extracellular LAB proteinase and not the consequence of the activities of the peptidases. LAB display a unique cell wall associated proteinase which is performing the first step in the degradation of proteins. However, many peptidases are located in the cytosol of the bacteria and membrane leakage could be responsible for their release in the fermentation medium.

The conversion of leucine p-nitroaniline to p-nitroaniline catalyzed by leucine aminopeptidase was measured in the samples that were previously analyzed by SDS-PAGE and ELISA.

This analysis demonstrated that little aminopeptidases were released from the cytosol of the bacteria into the medium during caseinate hydrolysis.

The overall hydrolysis of caseins by aminopeptidases was relatively low, reaching approximately 1% after 5 hours fermentation. Hydrolysis of caseins was thus resulting quasi exclusively from the serine-type extracellular bacterial proteinase.

Characterization of the Peptide Library

The casein-derived peptide library generated by *Lb. helveticus* CNCM I-2864 was characterised using liquid chromatography in combination with mass spectrometry.

Fractionation by HPLC

The strategy chosen for the fractionation of caseinate hydrolysates was set up in two steps.

A first fractionation occurred on a molecular weight basis by gel permeation chromatography. The second fractionation was based on the hydrophobic interactions of the casein-derived peptides with a $C_8$-reverse phase chromatography column.

Superdex 75 Gel Permeation Chromatography (GPC)

With a molecular weight standard, retention times were experimented on the Superdex 75.

Finally, seven fractions were collected after separation of the caseinate hydrolysate using size exclusion chromatography.

TABLE 1

Result of the first fractionation step achieved with
Superdex 75 gel permeation chromatography (GPC)

| | Name of Fraction | | | | | | |
|---|---|---|---|---|---|---|---|
| | $F^{ion}1$ | $F^{ion}2$ | $F^{ion}3$ | $F^{ion}4$ | $F^{ion}5$ | $F^{ion}6$ | $F^{ion}7$ |
| Retention Time [min] | 13.8-15.2 | 15.2-16.7 | 16.7-20.5 | 20.5-26.4 | 26.4-32.2 | 32.2-39.0 | 39.0-65.0 |
| Molecular weight range [Da] | 45,000-40,000 | 40,000-35,000 | 35,000-25,000 | 25,000-15,000 | 15,000-5,000 | 5,000-1,000 | <1,000 |

C8-Reverse Phase Chromatography

Fractions 6 (5-1,000 Da) and 7 (<1,000 Da) from GPC were further fractionated using reverse-phase chromatography.

Reverse-phase chromatography was used in combination with mass spectrometry for the characterization of the sample. The HPLC flow was directed to a micro flow-splitter with 10% going to the MS and 90% being collected in a fraction collector. Mass spectrometric analysis and collection of fractions were thus performed in the same run, allowing the determination of the exact qualitative peptidic composition of each collected fraction. Thirty-two fractions were collected as a function of the time, every 2.5 min.

Reverse-phase separation led to the identification of around five hundred peptides. All peptides were analyzed and characterised using mass spectrometric analysis and in particular MS/MS data.

Mass-Spectrometric Characterization of the Low Molecular Weight Peptide Fractions of the Hydrolysates Reverse-phase HPLC in conjunction with ESI-MS detection of casein-derived peptides in fractions 6 and 7 from GPC resulted in the identification of more than five hundred peptides.

Fragmentation patterns of peptides were obtained by MS/MS analysis of the most intense ions. To perform protein identification, mass spectrometry fragmentation patterns were used to search protein database. This work was done using the SEQUEST browser software. This tool was able to convert the character-based representation of amino acid sequences in a protein database to fragmentation patterns that were compared against the MS/MS spectrum generated on the target peptide.

The algorithm initially identified amino acid sequences in the database that matched the measured mass of the peptide, compared fragment ions against the MS/MS spectrum, and generated a preliminary score for each amino acid sequence. A cross correlation analysis was then performed on the top 500 preliminary scoring peptides by correlating theoretical, reconstructed spectra against the experimental spectrum. Best scores and the corresponding peptides were then proposed.

Fragmentation pattern showed predominance of the products ions at m/z 1053.3 and at m/z 730.8. These two intense signals correspond to fragments issued from internal cleavage near the proline; the strongest signal corresponding to the extension from the proline in the direction of the C-terminus. Moreover, we saw generation of both the b-type ($b_2$; m/z 292.2, $b_3$; m/z 421.4, $b_5$-$b_7$; m/z 617.7, 730.8, 787.9, $b_9$-$b_{11}$; m/z 984, 1140.3, 1197.4 and $b_{13}$; m/z 1441.7) and y-type ($y_3$-$y_{14}$; m/z 342.5, 489.6, 586.8, 643.8, 800.0, 899.1, 996.2, 1053.3, 1166.5, 1256.6, 1362.7, 1491.8) ions. These types of ions are predominantly generated in low energy collision induced dissociation.

All this information demonstrates the validity of the proposed peptide sequence. It was processed in a similar way for all characterised peptides. Fragmentation patterns with no clear assignable b- or y-type ions were rejected.

The characterization of the peptide library using mass spectrometry allowed the identification of five hundred low molecular weight peptides.

In conclusion, we have the confirmation that the *Lb. helveticus* CNCM I-2864 strain is able to generate peptides displaying bioactivity, as shown in the table above. This strain generated also more than five thousand low molecular weight peptides, all characterised by mass spectrometry. This peptide library, including peptides from two to twenty-eight amino acids, displayed also a new bioactive potential, as will be shown later.

The peptide library generated in this work is not as wide as a random synthetic peptide library or even as a phage display library. The identified peptides however cover the complete protein sequence of the caseins. Proteolytic peptide libraries obtained with enzymes that show a broad specificity have the advantage to generate peptides of different length with overlapping amino acid sequences, thus increasing the chances of positive hits.

Biological Activity of Caseinate Hydrolysates Cellular Proliferation Tests

The effect of caseinate hydrolysate on human colon cancer cell line HT-29 was investigated. This experimental set-up provides an experimental model in which it is possible to study, directly on the cells, the effects of fermented milk or fermented milk fractions.

For the first screening, HT-29 cells were incubated 24 hours with caseinate hydrolysates fermented for one, two and five hours with *Lb. helveticus* CNCM I-2864. All assays were performed in triplicate. Cell number was determined before and after incubation with caseinate hydrolysate, allowing the distinction between inhibition of cell proliferation and induction of cell death.

The observed cell growth of HT-29 in cellular culture medium without serum was normalized. As positive control, cells were incubated in presence of foetal calf serum, this serum containing various growth factors. Finally, as negative control, cells were incubated 24 hours in physiological saline, without any cellular culture medium. After 24 hours incubation with the samples, the cells were dyed using neutral red.

Indeed, the supravital stain neutral red is weakly cationic and is thus actively concentrated by viable cells in intracytoplasmic vacuoles and granules by binding to anionic sites. It has been described as a convenient and reproducible assay to determine cell proliferation in 96-well plates.

TABLE 2

Effect of caseinate hydrolysates on growth of HT-29 cells. Results are expressed as percentage of OD (OD measured at 540 nm) with respect to the control (−serum).

|  | +serum | −serum | 0.9% NaCl | Caseinate | Tris maleate | CNCM I-2864 oh | CNCM I-2864 1 h | CNCM I-2864 2 h | CNCM I-2864 5 h |
|---|---|---|---|---|---|---|---|---|---|
| % prolif | 112 +/− 17 | 100 +/− 9 | −26 +/− 8 | 93 +/− 12 | 72 +/− 13 | 83 +/− 5 | 23 +/− 5 | 26 +/− 3 | 104 +/− 10 |

As complementary controls, it was checked that neither sodium caseinate, the initial substrate, nor tris-maleate, the buffer used during caseinate hydrolysis had any negative effect on HT-29 cellular proliferation.

As we see from the data, sodium caseinate as well as tris-maleate had no activity towards cellular proliferation.

However, caseinate hydrolysates fermented for one and two hours showed high antiproliferative activity. This activity disappeared after 5 hours hydrolysis.

This particular feature indicates that some antiproliferative factors were generated during caseinate hydrolysis. They were then at their turn digested, and lost their bioactivity, explaining the disappearance of the antiproliferative properties of the caseinate hydrolysate at five hours fermentation. Thus antiproliferative factors present in the hydrolysates are probably of proteinic origin.

This hypothesis was examined. A fraction showing antiproliferative activity was tested in parallel with the same fraction having been digested successively by alcalase and proteinase A, two commercially available enzymes.

If we make the assumption that the responsible factor is of proteinic origin, heating the sample could induce a change in the conformation of active proteins, leading to the non-recognition of the mentioned protein by a putative receptor involved in cellular proliferation mechanism. Thus, the active fraction was submitted to heating, without enzymatic treatment. The effect on cellular proliferation of this heated fraction was in all points similar to the ones of the non-heated hydrolysate. To reject any interference of the heat-inactivated enzymes in the test, the active fraction was mixed with heat-inactivated enzymes and the activity of the sample remained unaffected.

At this stage, we were not able to differentiate between an active proteinic factor generated by the lactic acid bacteria strain during caseinate hydrolysis or a casein-derived peptide. This differentiation will be made when mass spectrometric analysis of the samples will be performed.

TABLE 3

Effect of caseinate hydrolysates on growth of HT-29 cells. Results are expressed as percentage of OD (OD measured at 540 nm) with respect to the control (−serum).

|  | +serum | −serum | 0.9% NaCl | Caseinate | CNCM I-2864 1 h | CNCM I-2864 1 h, ΔT | (E, ΔT) + CNCM I-2864 1 h | (CNCM I-2864 1 h + E) ΔT |
|---|---|---|---|---|---|---|---|---|
| % prolif | 121 +/− 4 | 100 +/− 8 | 5 +/− 5 | 93 +/− 7 | 28 +/− 12 | 13 +/− 12 | 13 +/− 6 | 100 +/− 13 |

CNCM I-2864, 1 h: caseinate hydrolysate fermented for one hour with the *Lb. helveticus* CNCM I-2864 for one hour;
CNCM I-2864 1 h, (E, ΔT): heat-treated caseinate hydrolysate;
(E, ΔT) CNCM I-2864 1 h: non-treated caseinate hydrolysate with addition of heat-inactivated enzyme;
(CNCM I-2864 1 h + E) ΔT: caseinate hydrolysate further hydrolysed with enzymes and finally heat-treated for enzyme inactivation.

The data presented in Table 2 show the effect on the proliferation of the colon cancer cell line HT-29 of an active fraction which has been further digested by commercially available enzymes. The enzymes were inhibited by heating.

In this specific experiment, the caseinate fraction fermented for one hour with *Lb. helveticus* CNCM I-2864 showed a reproducible inhibiting effect with 72% (previously 77%) inhibition of proliferation.

The same fraction, that had undergone further enzymatic treatment with alcalase and proteinase A, lost its antiproliferative character.

In order to establish the validity of this result, we checked that the final heating step was not responsible for the loss of bioactivity.

Casein-Derived Hydrolysates are not Cytotoxic

To be sure that the antiproliferative effect observed on the human colon cancer cell line was not the observation of the induction of necrosis, cytotoxicity tests were performed.

Most current assays for measuring cytotoxicity are based on alterations of plasma membrane permeability and the consequent release of cytoplasmic enzymes or the uptake of dyes, normally excluded by viable cells. We here chose to measure the lactate dehydrogenase (LDH) activity released from damaged cells.

TABLE 4

Determination of the cytotoxic potential of caseinate hydrolysates on HT-29 cells. Results are expressed as percentage of OD (OD measured at 490 nm) with respect to the control (lysate).

|  | Lysate | +serum | −serum | Caseinate | Tris maleate | CNCM I-2864 0 h | CNCM I-2864 1 h | CNCM I-2864 2 h | CNCM I-2864 Sh |
|---|---|---|---|---|---|---|---|---|---|
| % prolif | 100 +/− 8 | 4 +/− 2 | 0 +/− 6 | 9 +/− 3 | −1 +/− 4 | −6 +/− 6 | −4 +/− 7 | −6 +/− 3 | −7 +/− 3 |

No LDH activity was detected in any culture media of cells incubated 24 hours with caseinate hydrolysates. Based on this test, we may affirm that sodium caseinate hydrolysates did neither alter cell permeability nor induced necrosis.

Little LDH activity was however observed when cells were incubated in physiological saline only, showing that slight membrane alterations occurred as the result of harsh culture conditions.

Thus, considering these last results, we knew that sodium caseinate hydrolysates inducing a decreased colon cancer cell line proliferation were not cytotoxic.

Inhibition of Cell Proliferation by GPC Fractions

Considering the results of the first proliferation test, we have seen that hydrolysates fermented for one and two hours with *Lb. helveticus* CNCM I-2864 had antiproliferative character.

In Table 5 we present the cellular growth experienced when testing fractions of a caseinate hydrolysate fermented for two hours and separated on a molecular weight basis.

subfractions derived from a sample having shown antiproliferative activity, but absent in a sample not having exhibited bioactivity.

This search was effected and the results are presented in FIG. 1. Two potential candidates were identified, one sequence was derived from alpha-S1 and the other from beta casein.

Peptides from the candidate region retrieved in an inactive fraction are shown in black whereas peptides characterised in subfractions twenty-four to twenty-seven and showing activity are shown in gray.

Decision was taken to synthesize chemically the candidate active regions.

| Alanine | Ala | A |
| Arginine | Arg | R |
| Asparagine | Asn | N |

TABLE 5

Effect of caseinate hydrolysate's gel chromatography fractions (two hours fermentation) on growth of HT-29 cells. Results are expressed as percentage of OD (OD measured at 540 nm) with respect to the control (−serum).

|  | +serum | −serum | 0.9% NaCl | F1 | F2 | F3 | F4 | F5 | F6 | F7 | C2 rec. |
|---|---|---|---|---|---|---|---|---|---|---|---|
| % prolif | 122 +/− 9 | 100 +/− 13 | 13 +/− 9 | 97 +/− 7 | 108 +/− 11 | 95 +/− 15 | 102 +/− 19 | 104 +/− 19 | 54 +/− 8 | 62 +/− 12 | 29 +/− 10 |

F1: 45,-40,000 Da peptides;
F2: 40-35,000 Da;
F3: 35-25,000 Da peptides;
F4: 25,-15,000 Da peptides;
F5: 15-5,000 Da peptides;
F6: 5-1,000 Da peptides;
F7: peptides >1,000 Da.
C2 Reconst: fraction reconstituted on the basis of F1-F7.

Fractions F1 to F5 from GPC represent peptides with molecular weights ranging from 45 to 5,000 Da. These fractions did not contain any antiproliferative factors or these were present in insufficient quantity for detection.

On the contrary, F6 from GPC (corresponding to peptides: 5-1,000 Da) and F7 from GPC (peptides<1,000 Da) showed important antiproliferative activities and were further investigated.

We notice moreover that isocratic fractionation using neutral ammonium acetate solution is a mild technique ensuring biological activity's preservation. Indeed, we did not loose biological activity through separation of the hydrolysate as a reconstituted fraction (C2 Reconst.) showed identical activity as before separation (Table 4).

Samples were analyzed by mass spectrometry. We knew the exact peptidic content of each subfraction. Fractions showing antiproliferative potential, but inactive fractions too were characterised using mass spectrometry. Thus we searched for a peptidic sequence present in all slightly active -continued

| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Peptide Synthesis

Peptides sequences VENLHLPLPLL (SEQ ID NO:18), ENLHLPLPLL (SEQ ID NO:19), NLHLPLPLL (SEQ ID NO:12) and LNENLLRFFVAPFPEVFG (SEQ ID NO:20), NENLLRFFVAPFPEVFG (SEQ ID NO:21), ENLLRFFVAPFPEVFG (SEQ ID NO:22), FVAPFPEVFG (SEQ ID NO:23) were chemically synthesized by Dr. A. Razaname at the EPFL, Lausanne using the Fmoc-solid phase peptide synthesis strategy.

It was for chemical practical purposes that the alpha-S1 casein sequence was elongated at the C-terminus from phenylalanine to glycine.

Inhibition of Proliferation by Synthetic Peptides

Synthetic peptides that were tested on HT-29 cell line confirmed their antiproliferative potential.

The tested peptide LNENLLRFFVAPFPEVFG (SEQ ID NO:20) ($\alpha_{S1}$ 31-48) strongly inhibited proliferation (Table 6). The same experiment was performed with a shorter version of the former mentioned peptide: ENLLRFFVAPFPEVFG (SEQ ID NO:22) ($\alpha_{S1}$ 33-48). Best antiproliferative result s were obtained at two to four micromolar concentrations, giving an antiproliferative pattern similar to the one observed for LNENLLRFFVAPFPEVFG (SEQ ID NO:20) (data not shown). On the basis of this data and for this particular sequence, N-terminus elongation was shown to preserve biological activity.

TABLE 6

Effect on growth of HT-29 cells of the alpha- S1 derived synthetic peptide: LNENLLRFFVAPFPEVFG (SEQ ID NO: 20) ($\alpha_{S1}$ 31-48). Results are expressed as percentage of counts with respect to the control.

| | Peptide concentration [µM] | | | | | | |
|---|---|---|---|---|---|---|---|
| | 0 | 133 | 66 | 33 | 17 | 8 | 4 | 2 |
| % prolif | 100 | 135 | 119 | 131 | 114 | 160 | 44 | 56 |

In Vitro Inhibition of MMPs

We chose to focus attention on MMP-2, -7 and -9. First, MMP-9 is involved in breast, colorectal, lung, prostate, pancreatic and ovarian tumors. Its expression is closely associated with the conversion from radial growth phase to vertical growth phase and subsequent metastasis. Secondly, MMP-2 is involved in breast, colorectal, lung, prostate, pancreatic and ovarian tumors. Its increasing expression indicates progressing tumor grade. Finally, MMP-7 is involved in breast, colorectal, lung and prostate tumors. MMP-7 has been implicated in the early steps of tumor development.

Both families of synthetic peptides were tested for their potential as MMP inhibitors: the four peptides derived from casein alpha-S1 and the three derived from beta caseins.

As positive control we tested o-phenantroline, a broad metalloproteinase inhibitor, which showed complete MMP inhibition at 10 mM concentration (data not shown).

Inhibition data concerning MMP-2, MMP-7 and MMP-9 inhibition (Table 7) showed increasing inhibiting activities with increasing N-terminal length of peptides derived from beta casein.

Concerning MMP-2 and MMP-7, we observe an increasing inhibitory potential with N-terminal elongation of the ENLLRFFVAPFPEVFG (SEQ ID NO:22) sequence. However, this tendency is not confirmed in the case of MMP-9. Moreover, FVAPFPEVFG (SEQ ID NO:23) showed an equal inhibitory potential for all three MMPs tested.

In general, we might observe relatively large IC50 values differences between MMP-7 and MMP-9 or MMP-2. These differences might be explained by the structural variation between these enzymes. In fact, MMP-7 is lacking the hemopexin-like domain. This domain has been shown to play a functional role in substrate binding and/or in interactions with the tissue inhibitors of metalloproteinases (TIMPs), a family of specific MMP protein inhibitors.

TABLE 7

IC50 [µM] for the inhibition of MMPs using a flourescein conjugated gelatin

| | | $IC_{50}$ values [µM] | | |
|---|---|---|---|---|
| | | MMP-2 | MMP-7 | MMP-9 |
| Derived from beta casein | NLHLPLPLL (SEQ ID NO: 12) | 450 | 1200 | 600 |
| | ENLHLPLPLL (SEQ ID NO: 19) | 200 | 275 | 300 |
| | VENLHLPLPLL (SEQ ID NO: 18) | 150 | 250 | 300 |
| Derived from alpha-S1 casein | FVAPFPEVFG (SEQ ID NO: 23) | 500 | 300 | 400 |
| | ENLLRFFVAPFPEVFG (SEQ ID NO: 22) | 425 | 1000 | 150 |
| | NENLLRFFVAPFPEVFG (SEQ ID NO: 21) | 275 | 850 | 50 |
| | LNENLLRFFVAPFPEVFG (SEQ ID NO: 20) | 250 | 300 | 150 |

In Vitro Inhibition of ACE

It is important to notice that ACE belongs to the zincin family of proteinases containing the HEXXH short binding consensus sequence, the family including matrix metalloproteinases too.

Inhibitors of matrix metalloproteinases might thus interfere with other zinc-metalloproteinases. We decided to test MMP-inhibitory peptides for their ACE-inhibitory potential.

TABLE 8

IC50 [µM] for the inhibition of ACE using the synthetic tripeptide substrate N-[3-2(furyl) acryloyl]L-phenylalanylqlycylqlycine.

| | | $IC_{50}$ values [µM] ACE |
|---|---|---|
| Derived from beta casein | NLHLPLPLL (SEQ ID NO: 12) | 15 |
| | ENLHLPLPLL (SEQ ID NO: 19) | 250 |
| | VENLHLPLPLL (SEQ ID NO: 18) | 175 |
| Derived from alpha-S1 casein | FVAPFPEVFG (SEQ ID NO: 23) | 650 |
| | ENLLRFFVAPFPEVFG (SEQ ID NO: 22) | 250 |
| | NENLLRFFVAPFPEVFG (SEQ ID NO: 21) | 55 |
| | LNENLLRFFVAPFPEVFG (SEQ ID NO: 20) | 280 |

From the data of Table 7 and that of Table 8 we notice a similar behavior of alpha-S1 derived peptides concerning the inhibition of both ACE and MMP-9.

An identical behavior for the inhibition of MMP-9 and ACE was displayed by peptides derived from the beta casein sequence.

The data thus supports the features of the invention that are defined by the appended claims, and it is intended that such claims not be limited to the most preferred embodiment but that they be interpreted to cover the true spirit and scope of the invention to the fullest degree.

What is claimed is:

1. A metalloproteinases inhibitory agent comprising casein-derived peptides obtained by hydrolysis of casein by a food grade bacteria, wherein the agent is selected from the group consisting of isolated single-polypeptide-chain peptides set forth in SEQ ID Nos. 1, 3, 4, 5, 6 and 7, consisting of the amino acid sequence:

E-N-L-L-R-F-F-V-A-P-F-P-E-V-F, (SEQ ID NO: 1)

N-E-N-L-L-R-F-F-V-A-P-F-P-E-V-F, (SEQ ID NO: 3)

L-N-E-N-L-L-R-F-F-V-A-P-F-P-E-V, (SEQ ID NO: 4)

E-N-L-L-R-F-F-V-A-P-F-P-E, (SEQ ID NO: 5)

N-E-N-L-L-R-F-F-V-A-P-F-P-E, (SEQ ID NO: 6) and

G-L-P-Q-E-V-L-N-E-N-L-L-R-F-F. (SEQ ID NO: 7)

2. The agent of claim 1, in the form of a matrix-metalloproteinases inhibitory agent.

3. A method for systematical, local or topical inhibition of metalloproteinases, the method comprising treating the metalloproteinases with a metalloproteinases inhibitory agent of claim 1.

4. A toothpaste, mouth-wash, pharmaceutical or food product comprising the metalloproteinases inhibitory agent of claim 1.

5. The product of claim 4 comprising a fermented or non-fermented dairy product or beverage, a chewing-gum, candy, pet food or oral supplement.

6. A method of making a drug for reducing feline osteoclastic resorptive lesions, the method comprising incorporating in a suitable carrier the metalloproteinases inhibitory agent of claim 1.

7. A pharmaceutical composition comprising an effective amount of the metalloproteinases inhibitory agent of claim 1 for reducing activities and/or functions of metalloproteinases.

8. A method of providing treatment to a patient, the method comprising administering to the patient the metalloproteinases inhibitory agent of claim 1 for inhibiting cell proliferation in a disease selected from the group consisting of cancer, metastasis, tissue ulceration, arthritis or periodontitis.

9. A process for the manufacture of a metalloproteinases inhibitory agent, the process comprising:
preparing a solution comprising casein and a food grade bacteria, wherein the food grade bacteria comprises *Lactobacillus helveticus* CNCM I-2864,
holding the solution under conditions effective to partially hydrolyze the casein to provide a metalloproteinases inhibitory agent containing casein-derived peptides, and
stopping the hydrolysis by centrifugation to form the agent.

10. The process of claim 9, which further comprises recovering the inhibitory agent from the solution.

11. A process for the manufacture of a metalloproteinases inhibitory agent, the process comprising:
preparing a solution comprising casein and a food grade bacteria, wherein the food grade bacteria comprises *Lactobacillus helveticus* CNCM I-2864 and a bacteria selected from the group consisting of Lactobacilli and Bacilli and combinations thereof,
holding the solution under conditions effective to partially hydrolyze the casein to provide a metalloproteinases inhibitory agent containing casein-derived peptides, and
stopping the hydrolysis by centrifugation to form the agent.

12. An inhibitor of metalloproteinases comprising a peptide selected from the group consisting of isolated single-polypeptide-chain peptides set forth in SEQ ID Nos. 1, 3, 4, 5, 6 and 7, consisting of the amino acid sequence:

```
                                       (SEQ ID NO: 1)
E-N-L-L-R-F-F-V-A-P-F-P-E-V-F, (SEQ ID NO: 3)
N-E-N-L-L-R-F-F-V-A-P-F-P-E-V-F, (SEQ ID NO: 4)
L-N-E-N-L-L-R-F-F-V-A-P-F-P-E-V, (SEQ ID NO: 5)
E-N-L-L-R-F-F-V-A-P-F-P-E, (SEQ ID NO: 6)
N-E-N-L-L-R-F-F-V-A-P-F-P-E,
and
                                       (SEQ ID NO: 7)
G-L-P-Q-E-V-L-N-E-N-L-L-R-F-F.
```

* * * * *

SEQUENCE LISTING

<160> NUMBER OF SEQ ID NOS: 23

<210> SEQ ID NO 1
<211> LENGTH: 15
<212> TYPE: PRT
<213> ORGANISM: Bos taurus

<400> SEQUENCE: 1

Glu Asn Leu Leu Arg Phe Phe Val Ala Pro Phe Pro Glu Val Phe
1               5                   10                  15

<210> SEQ ID NO 2
<211> LENGTH: 20
<212> TYPE: PRT
<213> ORGANISM: Bos taurus

<400> SEQUENCE: 2

Glu Asn Leu Leu Arg Phe Phe Val Ala Pro Phe Pro Glu Val Phe Gly
1               5                   10                  15

Lys Glu Lys Val
            20

<210> SEQ ID NO 3
<211> LENGTH: 16
<212> TYPE: PRT
<213> ORGANISM: Bos taurus

<400> SEQUENCE: 3

Asn Glu Asn Leu Leu Arg Phe Phe Val Ala Pro Phe Pro Glu Val Phe
1               5                   10                  15

<210> SEQ ID NO 4
<211> LENGTH: 16
<212> TYPE: PRT
<213> ORGANISM: Bos taurus

<400> SEQUENCE: 4

Leu Asn Glu Asn Leu Leu Arg Phe Phe Val Ala Pro Phe Pro Glu Val
1               5                   10                  15

<210> SEQ ID NO 5
<211> LENGTH: 13
<212> TYPE: PRT
<213> ORGANISM: Bos taurus

<400> SEQUENCE: 5

Glu Asn Leu Leu Arg Phe Phe Val Ala Pro Phe Pro Glu
1               5                   10

<210> SEQ ID NO 6
<211> LENGTH: 14
<212> TYPE: PRT
<213> ORGANISM: Bos taurus

<400> SEQUENCE: 6

Asn Glu Asn Leu Leu Arg Phe Phe Val Ala Pro Phe Pro Glu
1               5                   10

<210> SEQ ID NO 7
<211> LENGTH: 15
<212> TYPE: PRT
<213> ORGANISM: Bos taurus

-continued

```
<400> SEQUENCE: 7

Gly Leu Pro Gln Glu Val Leu Asn Glu Asn Leu Leu Arg Phe Phe
1               5                   10                  15

<210> SEQ ID NO 8
<211> LENGTH: 23
<212> TYPE: PRT
<213> ORGANISM: Bos taurus

<400> SEQUENCE: 8

Phe Val Ala Pro Phe Pro Glu Val Phe Gly Lys Glu Lys Val Asn Glu
1               5                   10                  15

Leu Ser Lys Asp Ile Gly Ser
            20

<210> SEQ ID NO 9
<211> LENGTH: 8
<212> TYPE: PRT
<213> ORGANISM: Bos taurus

<400> SEQUENCE: 9

Leu His Leu Pro Leu Pro Leu Leu
1               5

<210> SEQ ID NO 10
<211> LENGTH: 9
<212> TYPE: PRT
<213> ORGANISM: Bos taurus

<400> SEQUENCE: 10

Leu His Leu Pro Leu Pro Leu Leu Gln
1               5

<210> SEQ ID NO 11
<211> LENGTH: 10
<212> TYPE: PRT
<213> ORGANISM: Bos taurus

<400> SEQUENCE: 11

Asn Leu His Leu Pro Leu Pro Leu Leu Gln
1               5                   10

<210> SEQ ID NO 12
<211> LENGTH: 9
<212> TYPE: PRT
<213> ORGANISM: Bos taurus

<400> SEQUENCE: 12

Asn Leu His Leu Pro Leu Pro Leu Leu
1               5

<210> SEQ ID NO 13
<211> LENGTH: 12
<212> TYPE: PRT
<213> ORGANISM: Bos taurus

<400> SEQUENCE: 13

Asn Leu His Leu Pro Leu Pro Leu Leu Gln Ser Trp
1               5                   10

<210> SEQ ID NO 14
<211> LENGTH: 15
<212> TYPE: PRT
<213> ORGANISM: Bos taurus
```

<400> SEQUENCE: 14

Asp Val Glu Asn Leu His Leu Pro Leu Pro Leu Leu Gln Ser Trp
1               5                   10                  15

<210> SEQ ID NO 15
<211> LENGTH: 10
<212> TYPE: PRT
<213> ORGANISM: Bos taurus

<400> SEQUENCE: 15

Val Glu Asn Leu His Leu Pro Leu Pro Leu
1               5                   10

<210> SEQ ID NO 16
<211> LENGTH: 9
<212> TYPE: PRT
<213> ORGANISM: Bos taurus

<400> SEQUENCE: 16

Val Glu Asn Leu His Leu Pro Leu Pro
1               5

<210> SEQ ID NO 17
<211> LENGTH: 25
<212> TYPE: PRT
<213> ORGANISM: Bos taurus

<400> SEQUENCE: 17

Leu Pro Leu Leu Gln Ser Trp Met His Gln Pro His Gln Pro Leu Pro
1               5                   10                  15

Pro Thr Val Met Phe Pro Pro Gln Ser
            20                  25

<210> SEQ ID NO 18
<211> LENGTH: 11
<212> TYPE: PRT
<213> ORGANISM: Bos taurus

<400> SEQUENCE: 18

Val Glu Asn Leu His Leu Pro Leu Pro Leu Leu
1               5                   10

<210> SEQ ID NO 19
<211> LENGTH: 10
<212> TYPE: PRT
<213> ORGANISM: Bos taurus

<400> SEQUENCE: 19

Glu Asn Leu His Leu Pro Leu Pro Leu Leu
1               5                   10

<210> SEQ ID NO 20
<211> LENGTH: 18
<212> TYPE: PRT
<213> ORGANISM: Bos taurus

<400> SEQUENCE: 20

Leu Asn Glu Asn Leu Leu Arg Phe Phe Val Ala Pro Phe Pro Glu Val
1               5                   10                  15

Phe Gly

<210> SEQ ID NO 21

-continued

```
<211> LENGTH: 17
<212> TYPE: PRT
<213> ORGANISM: Bos taurus

<400> SEQUENCE: 21

Asn Glu Asn Leu Leu Arg Phe Phe Val Ala Pro Phe Pro Glu Val Phe
1               5                   10                  15

Gly

<210> SEQ ID NO 22
<211> LENGTH: 16
<212> TYPE: PRT
<213> ORGANISM: Bos taurus

<400> SEQUENCE: 22

Glu Asn Leu Leu Arg Phe Phe Val Ala Pro Phe Pro Glu Val Phe Gly
1               5                   10                  15

<210> SEQ ID NO 23
<211> LENGTH: 10
<212> TYPE: PRT
<213> ORGANISM: Bos taurus

<400> SEQUENCE: 23

Phe Val Ala Pro Phe Pro Glu Val Phe Gly
1               5                   10
```